(12) United States Patent
Harada et al.

(10) Patent No.: US 8,419,751 B2
(45) Date of Patent: Apr. 16, 2013

(54) CLIP AND CLIPPING INSTRUMENT FOR BIOLOGICAL TISSUES

(75) Inventors: Shinetsu Harada, Akita (JP); Haruhiko Masuda, Akita (JP); Miyuki Nishimura, Okaya (JP); Akira Harada, Akita (JP); Yoshiaki Okada, Akita (JP)

(73) Assignee: Sumitomo Bakelite Company, Limited, Tokyo (JP)

( * ) Notice: Subject to any disclaimer, the term of this patent is extended or adjusted under 35 U.S.C. 154(b) by 839 days.

(21) Appl. No.: 12/500,884

(22) Filed: Jul. 10, 2009

(65) Prior Publication Data
US 2009/0275958 A1 Nov. 5, 2009

Related U.S. Application Data

(62) Division of application No. 10/548,835, filed as application No. PCT/JP2004/003468 on Mar. 16, 2004, now abandoned.

(30) Foreign Application Priority Data

| Mar. 17, 2003 | (JP) | 2003-072747 |
| Mar. 18, 2003 | (JP) | 2003-073655 |
| Jul. 3, 2003 | (JP) | 2003-190806 |
| Sep. 2, 2003 | (JP) | 2003-309507 |
| Mar. 5, 2004 | (JP) | 2004-061630 |

(51) Int. Cl.
*A61B 17/10* (2006.01)
*A61B 17/08* (2006.01)

(52) U.S. Cl.
USPC .................. 606/142; 606/139; 606/143

(58) Field of Classification Search .......... 606/139, 606/142, 143, 151, 157, 158, 1, 213, 232, 606/205–209; 604/57, 59; 623/6.12
See application file for complete search history.

(56) References Cited

U.S. PATENT DOCUMENTS 4,076,120 A 2/1978 Carroll et al.
5,445,167 A * 8/1995 Yoon et al. ............ 128/898
(Continued)

FOREIGN PATENT DOCUMENTS
JP 50-75797 11/1948
JP 62-189060 8/1987
(Continued)

*Primary Examiner* — Darwin Erezo
*Assistant Examiner* — Jing Ou
(74) *Attorney, Agent, or Firm* — Oblon, Spivak, McClelland, Maier & Neustadt, L.L.P.

(57) ABSTRACT

A clipping instrument for biological tissues equipped with an outer tube which can be inserted into a biological cavity, an operating member freely passed through the outer tube, an operating wire freely passed though the operating member, a self-opening holder which can be opened and closed by the action of the operating member attached to the edge of the operating wire, and a self-opening clop having a clipping member for clopping a biological tissue which is attached to the edge of the holder in a detachable manner by opening/ closing the holder. Using this clopping instrument, a lesion site can be surely clipped over a long period of time in ligating a breeding site in a biological tissue, stitching a laceration, making in excision of a mucosal tissue and so on with an endoscope.

7 Claims, 17 Drawing Sheets

U.S. PATENT DOCUMENTS

| | | | | |
|---|---|---|---|---|
| 5,520,701 | A | 5/1996 | Lerch | 606/142 |
| 5,634,932 | A | 6/1997 | Schmidt | 606/157 |
| 5,766,184 | A * | 6/1998 | Matsuno et al. | 606/142 |
| 5,766,189 | A * | 6/1998 | Matsuno | 606/158 |
| 6,814,742 | B2 * | 11/2004 | Kimura et al. | 606/151 |
| 7,740,639 | B2 * | 6/2010 | Hummel et al. | 606/142 |
| 7,806,903 | B2 * | 10/2010 | Shibata et al. | 606/142 |
| 8,080,021 | B2 * | 12/2011 | Griego | 606/143 |
| 8,133,273 | B2 * | 3/2012 | Aharoni et al. | 623/6.12 |
| 8,152,822 | B2 * | 4/2012 | Gayzik | 606/151 |
| 8,162,959 | B2 * | 4/2012 | Cohen et al. | 606/142 |
| 8,172,859 | B2 * | 5/2012 | Matsuno et al. | 606/142 |
| 2002/0045909 | A1 | 4/2002 | Kimura et al. | |
| 2007/0050023 | A1 * | 3/2007 | Bessiere et al. | 623/6.12 |

FOREIGN PATENT DOCUMENTS

| | | |
|---|---|---|
| JP | 62-170010 | 10/1987 |
| JP | 1-77703 | 5/1989 |
| JP | 2-6011 | 1/1990 |
| JP | 4-501676 | 3/1992 |
| JP | 07-008499 | 1/1995 |
| JP | 08-019548 | 1/1996 |
| JP | 11-513292 | 11/1999 |
| JP | 2000-15988 | 1/2000 |
| JP | 2000-335631 | 12/2000 |
| JP | 2001-520069 | 10/2001 |
| WO | WO 96/00033 | 1/1996 |

* cited by examiner

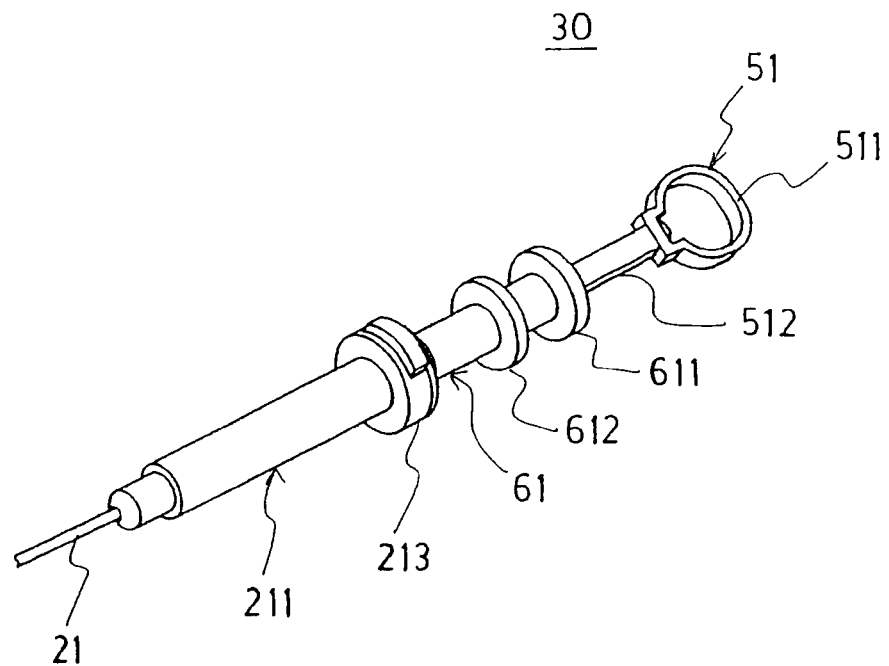
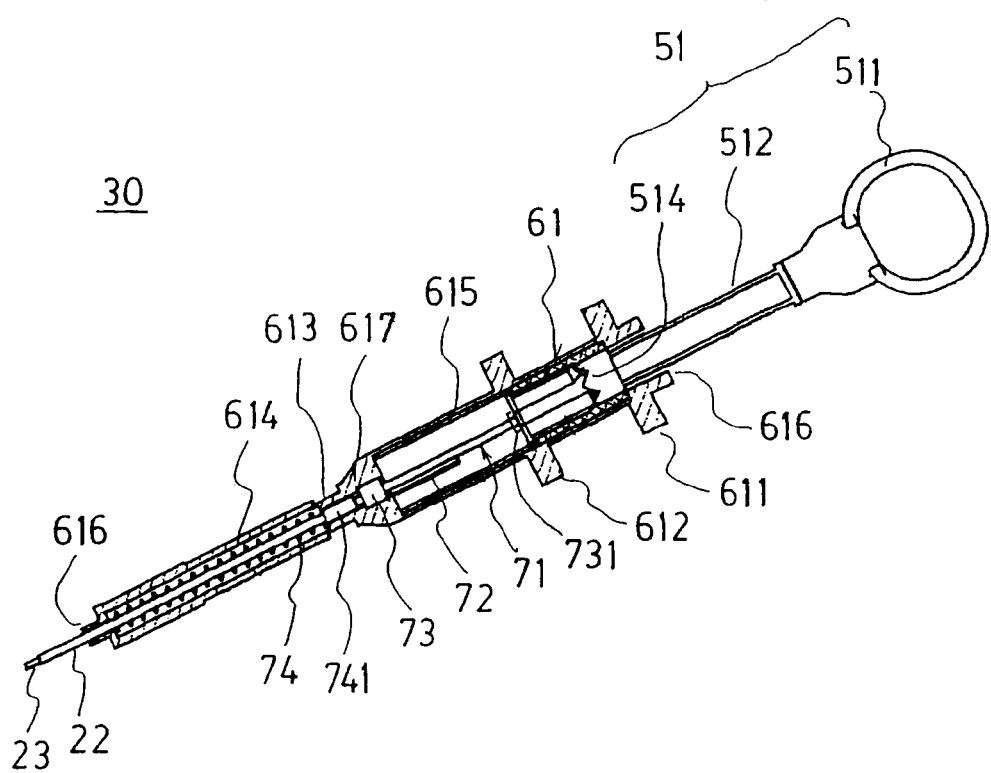
fig 11
fig 12

(A)

(B)

CLIP AND CLIPPING INSTRUMENT FOR BIOLOGICAL TISSUES

CROSS-REFERENCE TO RELATED APPLICATIONS

This application is a divisional of U.S. Ser. No. 10/548,835, filed Jun. 5, 2006, the contents of which are incorporated by reference herein in its entirety. U.S. application Ser. No. 10/548,835 is a national stage application of PCT/JP04/03468, filed on Mar. 16, 2004. This PCT application claims priority to Japanese patent application numbers: JP 2003-072747, filed Mar. 17, 2003; JP 2003-073655, filed Mar. 18, 2003; JP 2003-190806, filed Jul. 3, 2003; JP 2003-309507, filed Sep. 2, 2003; and JP 2004-061630, filed Mar. 5, 2004.

TECHNICAL FIELD

The present invention relates to a clip and a clipping equipment for biological tissues, which are used as a treating equipment for an endoscope for ligating a bleeding site in a biological tissue, stitching a laceration, and marking in excision of a mucosal tissue with an endoscope.

BACKGROUND TECHNIQUE

A clip used as a treating equipment for an endoscope is used in many cases, such as ligating a bleeding site, stitching a laceration, and marking in excision of a mucosal tissue with an endoscope. A clipping equipment for biological tissues disclosed in Japanese Utility Model Application Laid-Open (JP-U) No. 62-170010 is constructed of a clip 801 having opening habit, a clip securing ring 802 for closing a clip tip part, and a connecting plate 803 which is detachable on an operating wire in which a hook is attached to a tip (not shown), as shown in FIG. 35. In this clipping equipment 800 for biological tissues, when the clipping equipment holds a biological tissue such as a lesion, a connecting plate 803 is attached to a hook, an opened tip part of a clip 801 is pushed against a lesion with an endoscope, an operating wire positioned at a cavity of an operating member is pulled, thereby, a clip 801 is moved so that it is pulled into a clip securing ring 802, thereby, an opening part is closed to clip a lesion. And, since a clip 801 clips a lesion with an opening part on a tip side, a force directed to a basal direction of a clip 801 is exerted on a clip securing ring 802. However, when a biological tissue is ligated once, it is usually necessary to maintain the state where the tissue is clipped for about a few days to one week and, if a tissue immediately comes off, a tissue must be ligated again with a clip. Such the second time treatment is pain to a patient.

In addition, in order to prevent a connecting plate 803 from protruding from a clip securing ring 802, and preventing a clip 801 from coming out from a hook in the state where a clip 801 has not completely been closed, a gel-like fixing agent 804 is filled into a clip securing ring 802. However, it is difficult to fill into a cavity of a small clip securing ring 802 from a viewpoint of manufacturing and, upon clipping a biological tissue, there is a problem that a fixing agent 804 filled into a cavity of a clip securing ring 802 is peeled and fallen.

Japanese Patent Application Laid-Open (JP-A) No. 50-75797 discloses a tissue clipping equipment for grasping a tissue in a body with a clip using an endoscope, and dwelling the clip therein. Since in this clipping equipment, a clip is directly mounted on a hook provided on a tip of an operating wire, there is a problem that, when a clip is dwelled, a clipping equipment must be moved forwardly and backwardly, and left and right in order to remove a clip from a hook, thus, a way to use it is troublesome.

JP-U No. 2-6011 discloses a clipping equipment 900 which overcomes the aforementioned disadvantage, as shown in FIG. 36. This clipping equipment 900 is equipped with a hook 902 provided on a tip of an operating wire 901, and a connecting member 903 having an engaging pore 904 engaging with a pin 906 of a hook 902 on one end, and having a crook (not shown) which is connected to a clip and is deformable by stretching on the other end, wherein when a connecting plate 903 is moved to a hand side via an operating wire 901 in order to dwell a clip 905 in a biological tissue, a crook of a connecting plate 904 is stretched, and the engaging state of a clip 905 and a connecting plate 903 is released.

Although this clipping equipment 900 improved troublesome operation of removing a clip from a hook, since a connecting plate 903 is engaged with an operating wire 901 also after clip dwelling, a connecting plate 903 must be removed after taken out from an endoscope, and there is a problem of disposal of a connecting plate 903 which has become an unnecessary part. In addition, there is a problem that, since a connecting plate 903 is small, it is sucked into a sucking port of an endoscope rarely, and this becomes a cause for worse suction. In addition, as a common problem of clipping equipments described in JP-A No. 50-75797 and JP-U No. 2-6011, there is a problem that, when a clip is mounted on a clipping equipment, since a hook is a cantilevered type, balance is worse, and a clip is easily detached from a hook.

On the other hand, JP-U No. 1-77703 shows a clipping equipment in which a ratchet mechanism consisting of an engaging claw and a claw to be engaged of a ratchet is applied. This clipping equipment is such that a pitch of a claw to be engaged is formed finer than that of an engaging claw, or at least two sets of an engaging claw and a claw to be engaged are disposed, and a phase of one of them is shifted without altering a pitch of a claw, and a moving pitch is small-sized as a whole, in which by pulling a wire fixing a clip, and opening a clip to a greatest degree and further pulling a wire, a clip is closed and, finally, a connecting plate is destructed, releasing a clip.

According to this clipping equipment, a movement amount of an operating member can be operated finer by a ratchet mechanism. However, since attachment of a clip and operation of opening are performed by a ratchet mechanism, there is a problem that, in order to assuredly stop a clip at an intended position, an operator must perform position adjusting operation while seeing a clip, and operation is troublesome.

In addition, in a clipping equipment 900 described in JP-U No. 2-6011, since operation of engaging with a pin 906 of a hook and a small engaging pore 904 of a connecting plate 903 is performed in a dim endoscope chamber, it is difficult to mount a clip 905. In addition, since a handle is operated in the state where a pin 906 is engaged into an engaging pore 904, a pin 906 is detached during handle operation in some cases. Further, in many cases where a lesion must be grasped with a clip, it is difficult to perform rapid operation.

In addition, JP-A No. 2000-335631 discloses a clip packaging body for an endoscope in which a clip for an endoscope can be accommodated between substrates. According to this endoscope packaging body, when sterilization treatment is performed in a packaging body in advance, sterilization working becomes easy. However, in order to mount a clip on a clipping equipment from this clip packaging body for an endoscope, it is necessary to grasp a clip by one hand from above the packaging body in the state where a clip packaging body for an endoscope is opened half, so that a clip is not directly contacted with a hand, and hang a pin of a hook on a small engaging pore of a connecting plate in the state where two members of a handle and an operating member are grasped by the other hand. Such the operation needs a skill and is troublesome.

Therefore, an object of the present invention is to provide a treating equipment clip for an endoscope which can assuredly clip a lesion over a long period of time, in ligating a bleeding site of a biological tissue, stitching a laceration, and marking in excision of a mucosal tissue with an endoscope. In addition, another object of the present invention is to provide a clipping equipment for a biological tissue which does not need seeing a degree of opening of a clip and does not need fine positioning adjustment. In addition, other object of the present invention is to provide a clipping equipment for a biological tissue which does not need troublesome operation for mounting and removing a clip.

DISCLOSURE OF THE INVENTION

That is, the present invention provides a clip comprising a self-opening clip body having a clipping part on a tip and provided with a twin-arm part extending from a basal part, and a securing ring, wherein the self-opening clip body has a first concave part on a clip basal part, and a second concave part between the first concave part and a clip tip part, respectively, the securing ring is mounted on the first concave part, and is sliding-moved from a mounting position of a first concave part with an external force to be mounted on a second concave part, thereby, said clip is used as a treating equipment for an endoscope of closing a clipping part at a tip of the clip body.

Also, the present invention provides a clipping equipment for a biological tissue equipped with an outer tube which can be inserted into a biological cavity, an operating member freely passed through the outer tube, an operating wire freely passed through the operating member, and a self-opening holder which can be opened and closed by the action of the operating member attached to a tip of the operating wire.

Also, the present invention provides a clip holder having one or two or more clip accommodating grooves for accommodating a clip comprising a self-opening clip body having a clipping part on a tip and equipped with a twin-arm part extending from a basal part, and a securing ring freely moving in a tip direction which is mounted in a concave part of the basal part, in the state where said clip is sunk with its tip facing downwardly.

BRIEF DESCRIPTION OF THE DRAWINGS

FIG. 11 is a perspective showing a part of a clipping equipment for a biological tissue in a second embodiment, FIG. 12 is a cross-sectional view showing a part of a clipping equipment for a biological tissue of the present example.

BEST MODE FOR CARRYING OUT THE INVENTION

Figure 1:
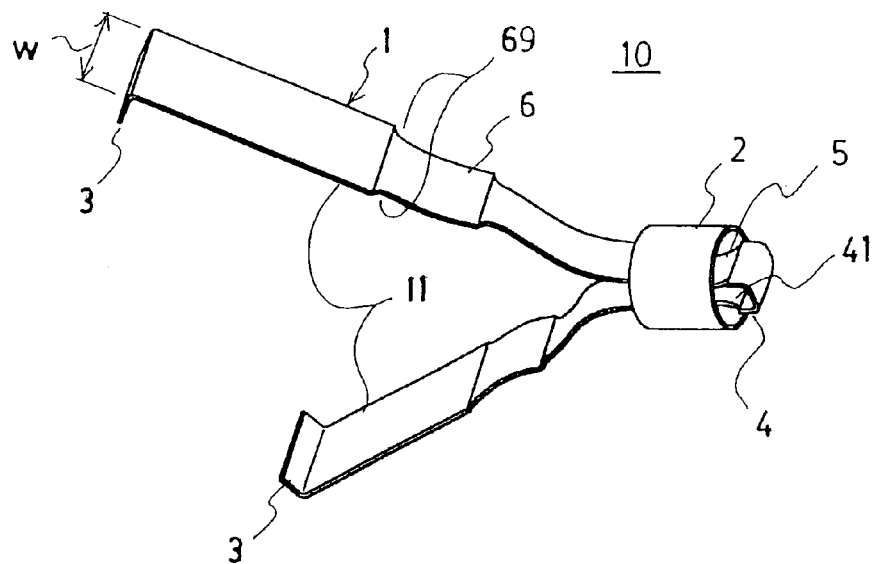
FIG. 1 is a perspective of a clip of an embodiment of the present invention.
Figure 2:
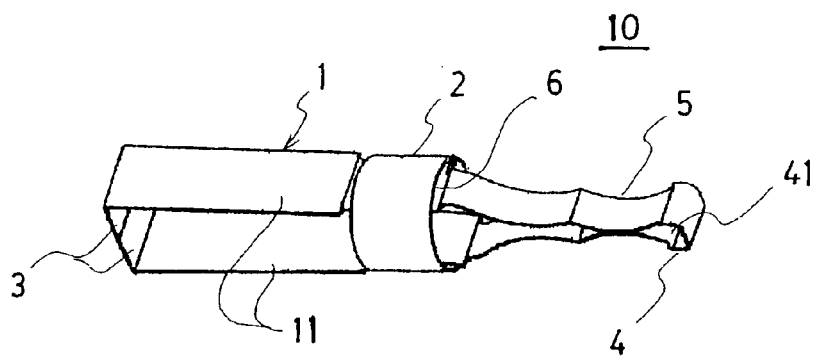
FIG. 2 is a view showing the closed state of a clip of FIG. 1.
Figure 3:
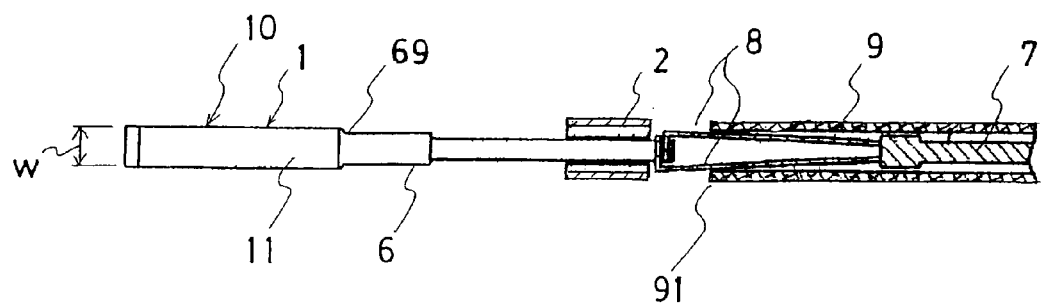
FIG. 3 is a cross-sectional view showing use aspect of a clip of FIG. 1.

In a clipping equipment for a biological tissue (hereinafter, simply also referred to as "clipping equipment") of the present invention and a clip, a tip side refers to a biological tissue side in the use state, and a basal side refers to a side opposite to a biological tissue. A clip in an embodiment of the present invention will be explained by referring to FIG. 1 to FIG. 3. As shown in FIG. 1 and FIG. 2, a clip 10 of the present example comprises a clip body 1 obtained by bending an elongate metal plate spring at a central part, and a cylindrical securing ring 2. A clip body 1 comprises clipping parts 3,3 for clipping a biological tissue on a tip, a basal part 4 exhibiting a generally U-shaped cross section, and twin-arm parts 11,11 having self-opening property on a tip which extend from a basal part 4. Since a metal plate spring constituting a clip body is movably inserted in a cavity of an operating member described later, a width size w thereof is restricted.

A clip body 1 has a first concave part 5 on a basal part 4, and second concaves 6,6 between a first concave part 5 and a clip tip part, respectively, and a securing ring 2 is mounted on a first concave part 5. As a site for mounting a first concave part 5 in a basal part, such a position is preferable that a space in which a tip of a holder 8 can be hung on a generally U-shaped cross-sectional part 41 is possessed, and opening of a clip tip in the opened state cannot be narrowed. In addition, a site for mounting a second concave part 6 is not particularly limited as far as it is between a first concave part 5 and a clip tip part, and clipping parts 3,3 of a clip tip are tightly abutted thereagainst. In the present example, by providing a plate width ramp 69 on a tip side of a second concave part 6, and making a basal side from a ramp 69 a concave part, when a securing ring 2 is sliding-moved from a mounting position in a first concave part 5 with an external force, it is assuredly mounted in a second concave part 6. It is preferable that a concave degree of a second concave part 6 of a clip body is larger than a concave degree of a first concave part 5 in that a securing ring 3 can be ensured. In addition, in clipping parts 3,3 at a clip tip, it is preferable that a tip part of a twin-arm part is bent inwardly and, at the same time, an irregular part is provided on its abutting surface in that a biological tissue can be tightly clipped.

In a clip 10, a holder 3 on a tip is usually opened as shown in FIG. 1 and, in this state, a securing ring 2 is mounted on a first concave part 5 of a basal part 4. Since a cavity part of a securing ring 2 is hung on a recess part, a securing ring 2 mounted in a first concave part 5 is not naturally moved forwardly and backwardly as far as an external force is exerted, and is not slipped on a tip side, not narrowing an opening width of a clipping part 3. Examples of a material for a clip include stainless steel, and titanium. In addition, a length of an arm part of a clip is not particularly limited, but is preferably 2.0 to 6.0 mm, particularly preferably 3.0 to 5.0 mm. When the length is within the aforementioned range, particularly, holding property of a clip is excellent.

Then, a method of clipping a biological tissue with a clip 10 will be explained. First, a pair of self-opening arm-like holders 8 which is attached to a tip of an operating wire 7 of a clipping equipment are hung on an internal side of a generally U-shaped cross sectional part 41 of a basal part 4 of a clip 1. Then, when an operating wire 7 which is in a cavity of an operating member 9 and can be moved forwardly and backwardly is pulled, holders 8 are pulled into a cavity of an operating member 9, and a securing ring 2 is abutted against a tip 91 of an operating member 9. By further pulling an operating wire 7, a twin-arm part 11 of an clip body is gradually pulled into a cavity of a securing ring 2 from a basal part side of a clip and, when pulled until a position of a second concave part 6, a step 69 and a securing ring 2 are abutted, thereby, a securing ring 2 is stopped, clipping parts 3,3 at a tip of a clip body 1 are abutted into the state where a biological tissue (not shown) is clipped (FIG. 2). Then, when an operating wire 7 is pushed in a direction opposite to pulling of an operating wire 7, that is, forwardly, a self-opening holder 8 is automatically come out from a basal part 4 of a clip. On the other hand, since a securing ring 2 is fixed firm in a recess part of a second concave part 6, a clip body 1 in the closed state can assuredly clip a biological tissue to be clipped regardless of a size thereof, the tissue is not come out therefrom, and the state where a biological tissue is clipped can be maintained over a long period of time.

As a material for a clip body 1, a metal such as stainless steel and a titanium alloy, and a plastic such as an ABS resin, a rigid vinyl chloride resin, polyamide and polyethylene are preferable in that they are not corroded in a cavity, particularly, in stomach in which a digestion enzyme is secreted. In addition, a material rich in elasticity is preferable in that, upon clipping of a biological tissue, a clipping part 3 at a clip tip is brought into the closed state from the opened state, and is it necessary to retain the closed state for a long period of time. In addition, a material for a securing ring is not particularly limited, but the ring is used together with a clip body 1, and examples of the material include the same material as that of a clip body 1. Specifically, a plastic such as fluorine resin, polyamine, and a silicone resin, and a metal such as stainless steel, and a titanium alloy are preferable.

According to a clip 10 of the present embodiment example, a biological tissue such as a lesion can be assuredly clipped over a long period of time.

A clipping equipment for a biological tissues in the first embodiment of the present invention will be explained by referring to FIG. 4 to FIG. 10. A clipping equipment 20 for a biological tissue in an embodiment of the present example is equipped with an outer tube 21 which can be inserted into a biological cavity, an operating member 22 freely passed through the outer tube 21, an operating wire 23 freely passed though the opening member 22, a self-opening holder 24 which can be opened and closed by the action of the operating member attached to a tip of the operating wire 23, and a self-opening clip 10a having a clipping member for clipping a biological tissue which is attached to a tip of the holder 24 in a detachable manner by opening/closing the holder. For example, a basal part of an operating wire 23 is connected to a handle (not shown).

In a clipping equipment 20 for a biological tissue, a material for an operating member 22 is not particularly limited, but examples include a thermoplastic resin such as polyether ether ketone, polyamide, and polyimide, and a thin metal coil. A thermoplastic resin is preferable in that it can assuredly transmit movement of an operating handle to a tip side, and a thin metal coil is preferable in that although a gap is formed by bending or pulling, bending property and rigidity are excellent. An external diameter of an operating member 22 is not particularly limited, but is preferably 1.7 to 2.7 mm, particularly preferably 1.9 to 2.3 mm.

An operating wire 23 has a holder 24 fixed at a tip, and has a connecting part 25 having a slightly larger diameter that of a wire body which is equipped with a step 26. In addition, at a position apart from a tip of an operating member 22 to a basal side by a stroke of an operating member, and on an internal wall of an operating member 22, a stopper 27 through which an operating wire body can inserted and which is abutted against a step 26 is attached, preventing excessive protrusion of an operating member 22, and preventing a holder 24 from excessively entering an operating member 22. A material for an operating wire 23 is not particularly limited, but a material, a whole or a part of which has flexibility, is preferable. Specific examples include a metal wire such as stainless steel, and carbon steel, and a resin fiber such as polyamide, polyether, and ultra high molecular weight polyethylene.

An outer tube 21 is a hollow continuous flexible member. An internal diameter of an external casing 21 is not particularly limited, but is preferably 1.8 to 2.8 mm, particularly preferably 2.0 to 2.4 mm. When an internal diameter is within the aforementioned range, operating property is particularly excellent. In addition, a length of an external casing 21 is not particularly limited, but is preferably 1,500 to 3,000 mm, particularly preferably 1,600 to 2,300 mm. When the length is within the aforementioned range, operating property in an endoscope is particularly excellent. A material for an external case 21 is not particularly limited, but examples include a fluorine resin such as polytetrafluoroethylene (PTFE), and a tetrafluoroethylene-hexafluoropropylene copolymer resin (FEP).

Figure 4:
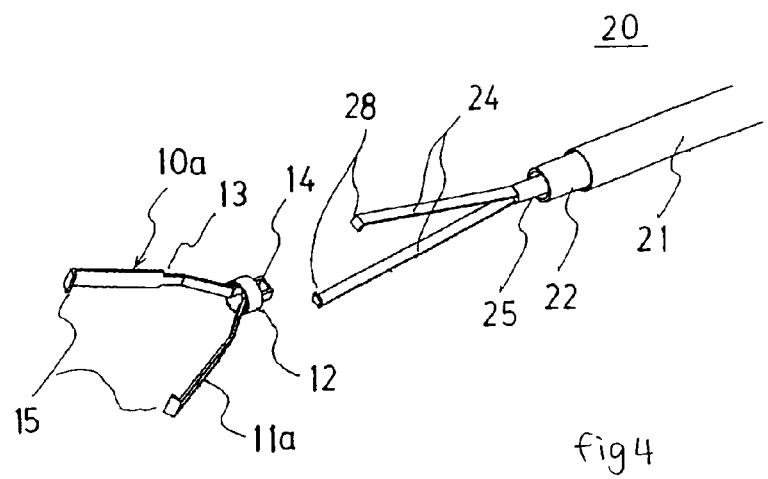
FIG. 4 is a perspective showing a part of a tip side of a clipping equipment for a biological tissue of the present example.

In a clipping equipment 20 for a biological tissue, a clip 10a is not particularly limited as far as it is equipped with a self-opening twin-arm part 11a, and a securing ring 12 for closing a clipping part 15 of a twin-arm part 11a as shown in FIG. 4, but a clip 10 shown in FIG. 1 and FIG. 2 is preferable.

Figure 6:
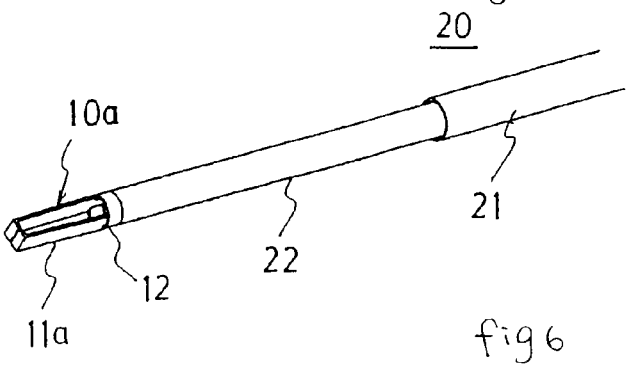
FIG. 6 is a view showing the state where a clip is closed.
Figure 7:
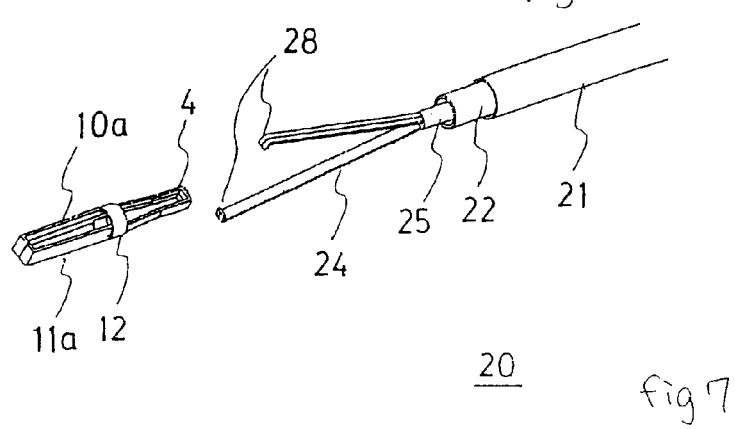
FIG. 7 is a view showing the state where a closed clip is detached.
Figure 8:
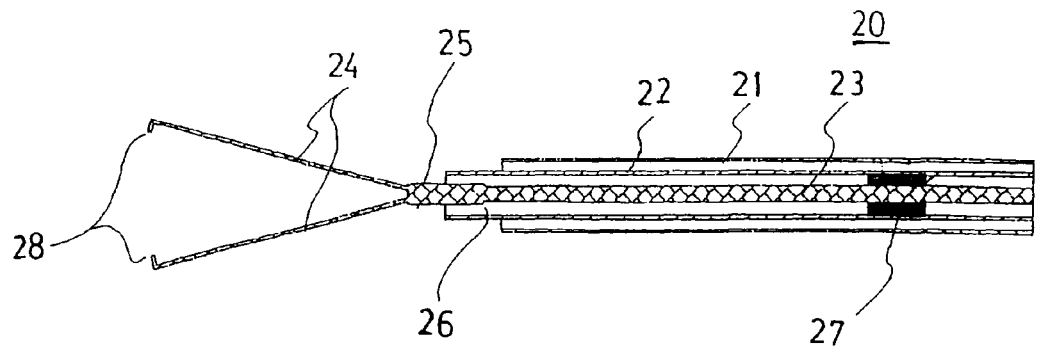
FIG. 8 is a cross-sectional view of a tip side of a clip equipment omitting description of a clip.
Figure 9:
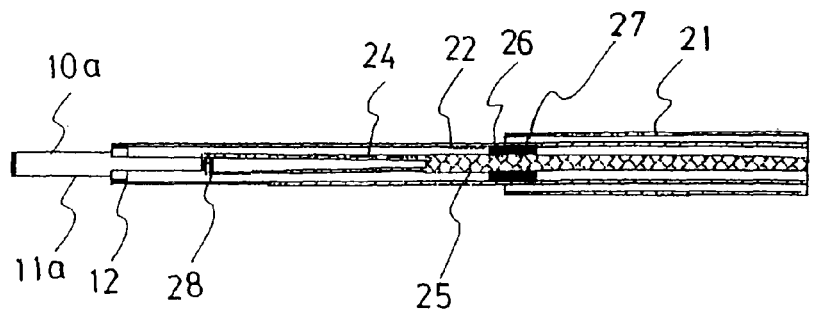
FIG. 9 is a longitudinal cross-sectional view of FIG. 6.

A method of mounting a clip 10a in a clipping equipment 20 for a biological tissue by the aforementioned construction will be explained. For example, in the state of FIG. 4, an operating wire 23 is fixed at an operating handle and, by pulling an operating handle, an operating member 22 is moved on a holder 24 side in a direction of an axis line of an operating wire 23. Thereby, a holder 24 consisting of a pair of arm parts enters a basal side while contacting with an internal circumferential surface of an operating member 22, therefore, is gradually being closed. And, a tip hook 28 of an operating member 22 is closed, clipping a basal part 14 of a clip 10a to retain a clip 10a. Further, by pulling an operating handle, a securing ring 12 is abutted against a tip of an operating member 22, and then a securing ring 12 is abutted against a step 13 which is between both arm parts of a clip 10a, closing clipping parts 15,15 of a clip (FIG. 6, FIG. 9). By returning an operating member 22 to an original position from this state, a holder 24 is protruded from an operating member 22, self-opening property possessed by a holder 24 makes a pair of arm parts in the opened state, and a clip 10a while it is opened can be detached.

According to a clipping equipment 20 for a biological tissue, complicated operating is not necessary in mounting or detaching a clip. In addition, when a clip 10a is retained by a holder 24, even if an operating member 22 is moved slightly, since a holder 24 is still accommodated in a cavity of an operating member 22, and tip hooks 28 are overlaid each other, a clip 10a is not easily fallen. In addition, even when a gap between tip hooks 28 is slightly opened, since a plate of a U-shaped cross section 41 of a basal part 4 of a clip 10a has an extent of a width, a clip 10a is not fallen from a holder 24.

Figure 10:
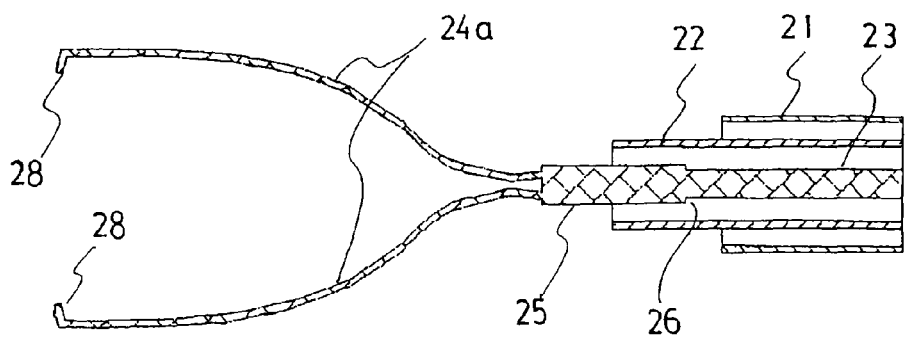
FIG. 10 is a view showing a variation example of a clipping equipment for a biological tissue of the present example.
Figure 13:
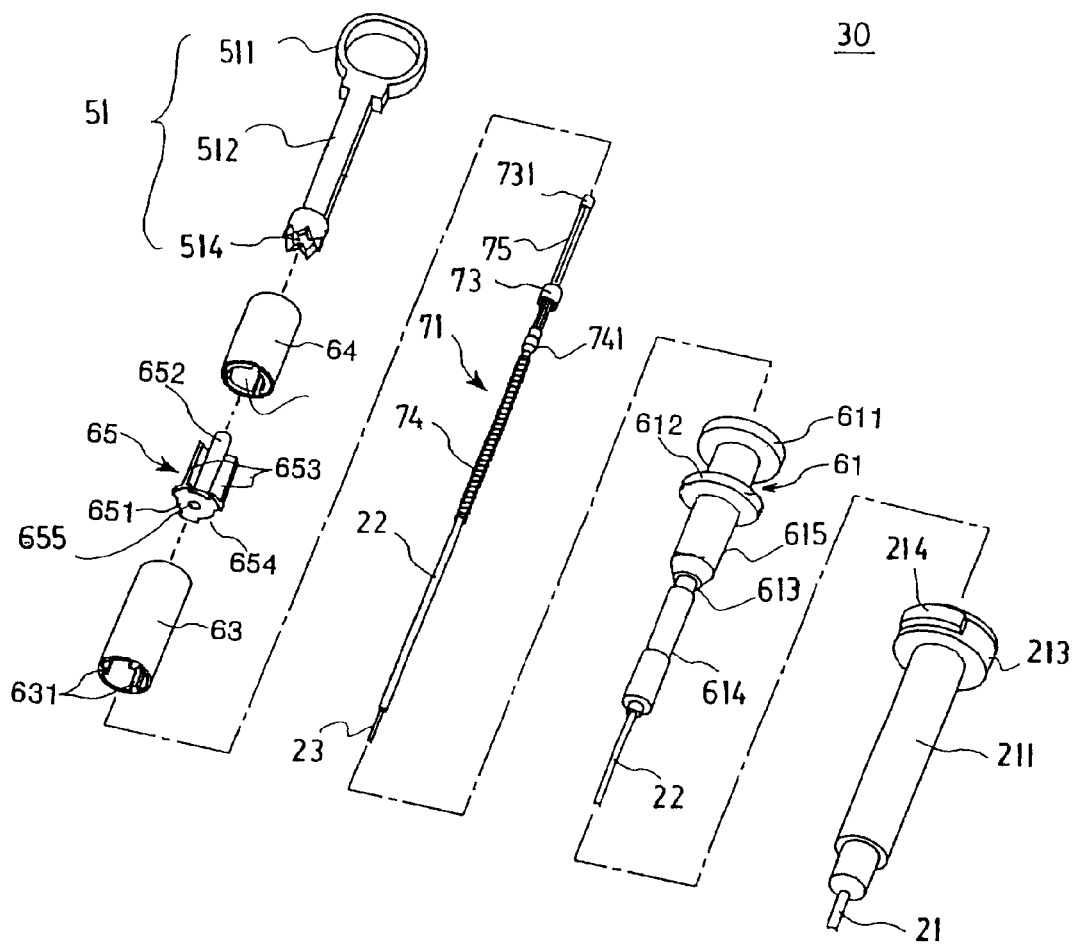
FIG. 13 is an exploded view of a clipping equipment for a biological tissue of the present example.
Figure 14:
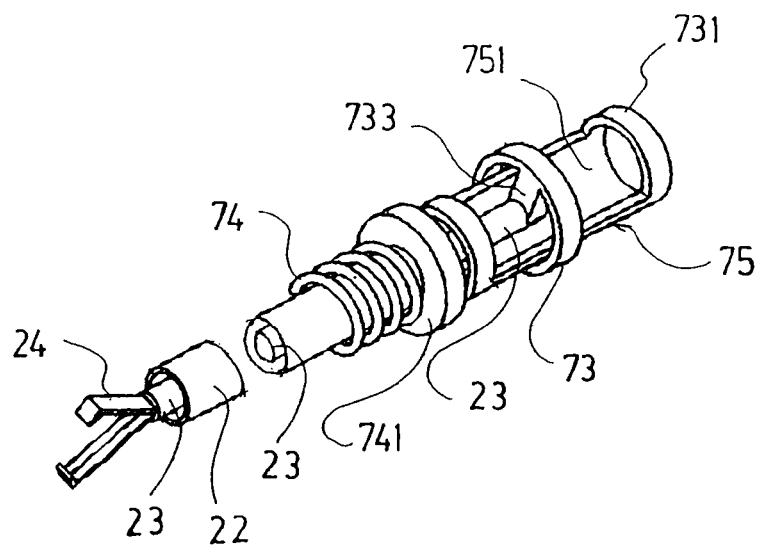
FIG. 14 is an enlarged view omitting a part of a bar-like member.
Figure 15:
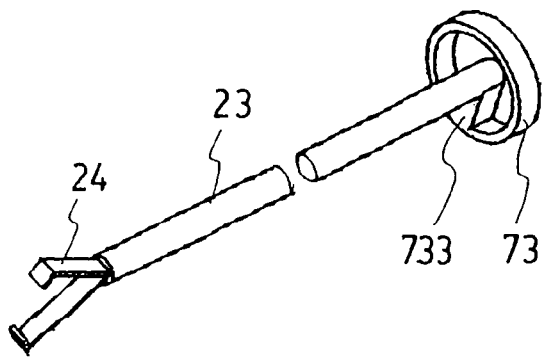
FIG. 15 is an enlarged view of an operating wire.
Figure 16:
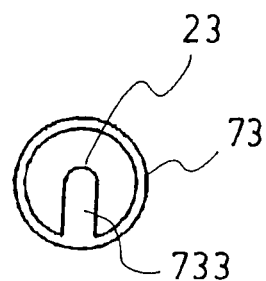
FIG. 16 is a view in which an operating wire of FIG. 15 is seen from an upper side, FIG. 17 (A) is a view showing an abutment relationship between an operating member and a sliding short casing, (B) is a view in which the equipment is seen along with an A-A line of (A), FIG. 18 (B) is a front view showing a part of a handle axis which is a member constituting a clip equipment of the present example (A) is a left side view of (B), FIG. 19 (B) is a front view of a rotation body which is a member constituting a clip equipment of the present example, (A) is a left side view of (B), (C) is a right side view of (B), FIG. 20 (B) is a front view of a position holding means which is a member constituting a clipping equipment of the present example, (A) is a left side view of (B), FIG. 21 (B) is a front view of a stopping means which is a member constituting a clipping equipment of the present example, (A) is a left side view of (B)
Figure 17:
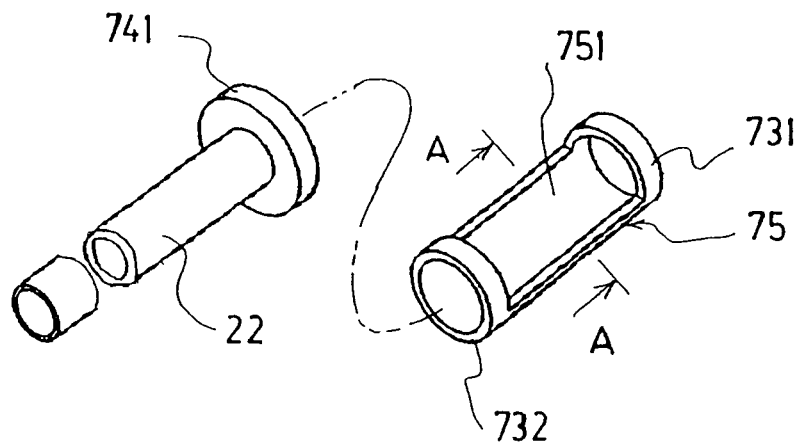
Figure 17:
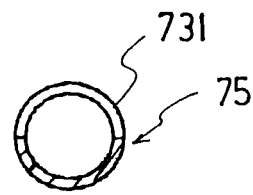
Figure 18:
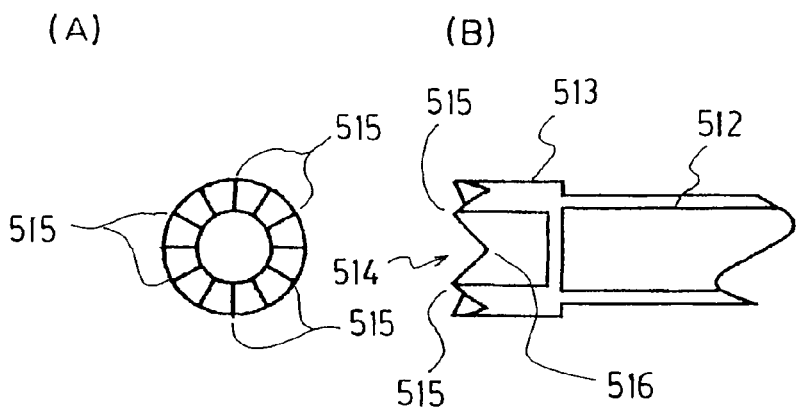
Figure 19:
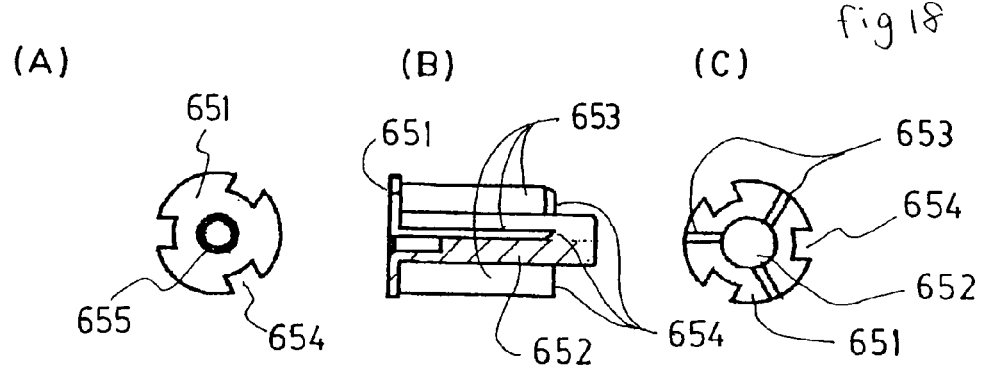
Figure 20:
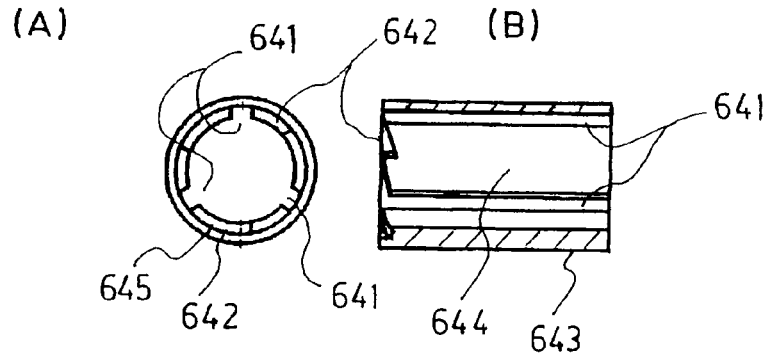
Figure 21:
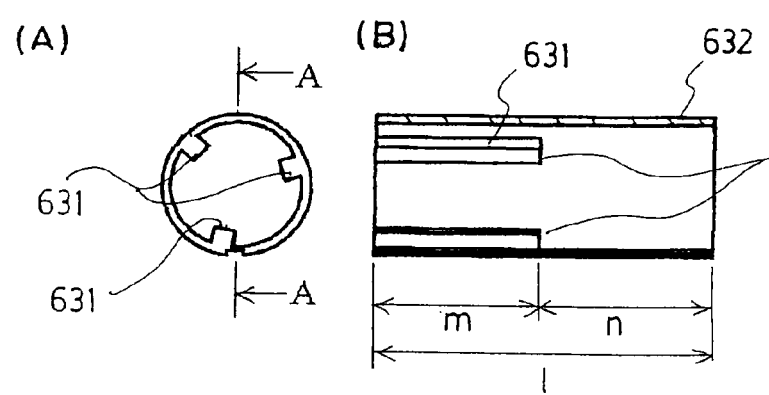

In a clipping equipment 20 for a biological tissue, a shape of a holder 24 is not limited to the aforementioned generally V-letter shape, but for example, a generally U-letter shape 24a as shown in FIG. 10 suffices. By curving an arm part of a holder 24a, a load applied to a connecting part 25 accompanied with shape change can be dispersed, spring characteristic is improved and, further, a tip part can be closed more rapidly as compared with a linear-like state. As a curved shape, any shape can be adopted in view of a time of opening and closing motion of a twin-arm part, and spring characteristic.

In addition, a method of operating member 22 and an operating wire 23 is not limited to the aforementioned method, but examples include a method of fixing an operating wire 23, and moving an operating member 22, and a method of moving both of an operating wire 23 and an operating member 22.

According to a clipping equipment 20 for a biological tissue, since complicating procedure such as mounting and detachment of a clip is not necessary, the equipment is extremely useful as a clipping equipment for a biological tissue which is used in marking for making clear a region where treatment such as ligation and excision of a bleeding site of a biological tissue.

Then, a clipping equipment for a biological tissue in a second embodiment will be explained by referring to FIG. 11 to FIG. 23. In FIG. 12, description of a sliding cylinder 211 of FIG. 11 is omitted. In a clipping equipment 30 for a biological tissue of the present example, the same symbol is added to the same component as that of the clipping equipment 20 for a biological tissue in the first embodiment example, explanation thereof is omitted, and different points will be mainly explained. That is, in a clipping equipment 30 for a biological tissue, a different point from a clip equipment 20 for a biological tissue is in that the equipment further has a handle 51 for controlling an operating member, and a first forcing mechanism for forwarding a handle 51 and, at the same time, stopping forwarding of a handle 51, a retaining mechanism for retaining a stoppage position of a handle 51 once, a second forcing mechanism for further forwarding from a stoppage position of a handle 51 and, at the same time, stopping forwarding of a handle, and a returning mechanism by which a handle 51 is automatically returned to a position before first forcing are provided. That is, a clipping equipment 30 consists of an external casing 21, a hollow sliding cylinder 211 which is connected to an external casing 21 on a tip side, and provided with a connecting flange 213 on a basal side, an equipment body part 61 equipped with a main chamber in which a tip side part is fitted into a cavity of a sliding cylinder 211, a stopping means situated on a tip side which is mounted in a main chamber of an equipment body part 61 in the fixed state, a position retaining means 64 which is mounted in a main chamber adjacent to a stopping means 63 on a basal side in the fixed state, a handle 51 which is inserted into an equipment body part 61 from a basal side, and a bar-like member 71 in which one end on a basal side is abutted against a back of a substrate 651 of a rotation body 65, and the other end is protruded from a tip side of an equipment body part 61.

A handle 51 consists of a ring-like clipping part 511, and a handle axis 512 in which one end is connected to a clipping part 511 and the other end is equipped with a crown-like first cam part 514. A clipping part 511 is operated by an operator by grasping with a hand, and has such an extent of a space that a finger of an operator can be inserted. A first cam part 514 is a ring-like projection having 6 triangular projections in which valley parts are formed every 60 degree on an end face of a cylindrical member. A first cam part 514 engages with three engaging feathers 653 of a rotation body 65 which moves in a stopping means 63 and in a position retaining means 64, and imparts a forwarding force and a rotating force to a rotation body 65. In the figure, for drawing reason, there is a different form around a connecting part of a ring-like clipping part 511 and a handle axis 512.

A position retaining means 64 is a cylindrical member which is fixed in a main chamber 615 of an equipment body part 61, determines a position of accommodation of a rotation body 65 in the state before operation, guides forwarding of a rotation body 65 by first forcing operation and, at the same time, leads a rotation body to a position of initiation of second forcing. On an internal circumferential surface 644, three fitting grooves 641 in which three plate-like feather members 653 of a rotation body 65 are fitted are formed along with a longitudinal direction. In addition, on a circumferential edge of an opening on a tip end, a cam group 642 equipped with 6 saw blade cross section-shaped notches 645 is attached. When a tip of a feather member 653 of a rotation body is abutted against an inclined surface of a notch 645 by spring power, a cam groove 642 imparts rotation of maximum 60 degree. An inclined surface of a notch 645 is formed as a descending inclination in a counterclock direction seen from a tip side.

A stopping means 63 is a cylindrical member which is fixed adjacent to a tip side of a position retaining means 64 in a main chamber of an equipment body part 61, stops a entering rotation body 65 by first forcing operation and, at the same time, guides entrance of a rotation body 65 by second forcing operation. A stopping means 63 has three ribs 631 extending from a tip side to a midway in an axial direction on an internal circumferential surface (length of symbol m of FIG. 22). Three ribs 631 are formed at an interval of 120 degree, and one rib is formed at a position at 50 degree counterclockwisely relative to a vertical axis seen from a tip side. A stopping means 63 is such that a tip opening is abutted against a wall of a main chamber in the state where it is disposed in a main chamber of an equipment body part 61. For this reason, a rotation body 65 is not protruded from a stopping means 63 in a tip direction. A length l of a stopping means 63 is a forwarding stroke of a rotation body 65.

A rotation body 65 is fitted with a first cam part 514 at a tip of a handle axis, and is forwarded, retreated or rotated in a position retaining means 64 and a stopping means 63 to transmit an operating force to a bar-like member 71. A rotation body 65 has a substrate 651 positioned at a tip side which has notches 654 at a 120 degree pitch, and a second cam part 654 having one end on a basal side thereof of a sharp cross section 656 shape with a plate-like feather member 653 which extends in an axial direction, at the same time, is attached at a 120 degree pitch between notches 654, on a substrate 651. In addition, the body has an engaging pore 655 with which a tip part 731 of a bar-like member 71 is engaged, on a center of a back of a substrate 651.

A bar-like member 71 has a holder 24 attached at a tip, and is equipped with an operating wire 23 in which a basal end is fixed at a fixing ring part 73, an operating member 22 having a cavity in which an operating wire 23 is inserted, and having a regulating part 741 on a basal end, and a sliding short casing 75 in which a window part 751 is formed on an external circumferential surface of a cylindrical casing abutting with a regulating part 741 on a basal side. A basal part 751 of a sliding short casing 75 is engaged with an engaging pore 655 on a back of a substrate 651 of a rotating body. A fixing ring part 73 is fixed on a tip side slightly from a main chamber of an equipment body part 61, and is not interlocked with operation of a handle. A fixing ring part 73 of an operating wire 23 is slidably fitted in a window part 751 of a sliding short casing 75. An operating member 22 is forwarded against spring power of a spring 74 via a sliding short casing 75 by forwarding of a rotation body 65 (forwarding of a handle 51) and, when a rotation body 65 is retreated by spring power of a spring 74, the member is retreated interlocking therewith. In addition, since an operating wire 23 is freely inserted into an operating member 22, and a connecting part 733 on a basal side is slided in a window part 751 of a sliding short casing 75, this is not interlocked with operation of a handle 51 (movement of an operating member 22).

An interior of an equipment body part 61 has, in an order from a tip side, a tip opening 616 in which an operating member 22 comes in and out, a chamber 614 for accommodating a spring 74, a fixing part 617 at which a fixing ring part 73 of a bar-like member is fixed, a main chamber 615 in which a stopping means 63 and a position retaining means 64 are accommodated, and an inserting port 616 in which a tip of a handle axis is inserted. In an equipment body part 61, a first flange part 611, and a second flange part 612 are attached to a cylindrical body from a basal side, to enhance operating property.

A sliding cylinder 211 is a member for operating forwarding and retreating of a hollow external casing 21, and is a cylindrical entity which is fitted at a tip part of an equipment body part 611. A tip side is connected to a hollow external casing 21 which is inserted into a biological cavity, and a fixing flange 213 having a convex part (not shown) fitting in a concave part 613 of an equipment body part is provided on a basal side. An engagement releasing means 214 for releasing engagement between a slide cylinder 211 and an equipment body 61 is attached to a fixing flange 213. An operating member 22 is inserted into an external casing 21. And, a sliding cylinder 211 mounted on an equipment body part 61 is such that, when operation of pulling a handle 51 in the state where engagement with an equipment body part 61 is released, or forcing a sliding cylinder 21 therein is performed, an external casing 21 is forwarded to an operating member 22. Thereby, a twin-arm part of a clip 10a is closed, and can be transiently accommodated in an external casing 21 in the state where a clip 10a is closed. Thereby, when an external casing 21 is inserted into an endoscope, since a clip 10a is accommodated in an external casing 21, a forceps pore of an endoscope is not damaged.

Figure 5:
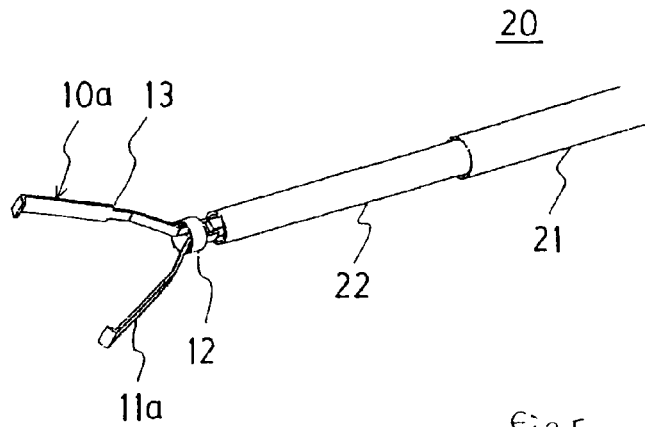
FIG. 5 is a view showing the state where a clip is mounted.
Figure 22:
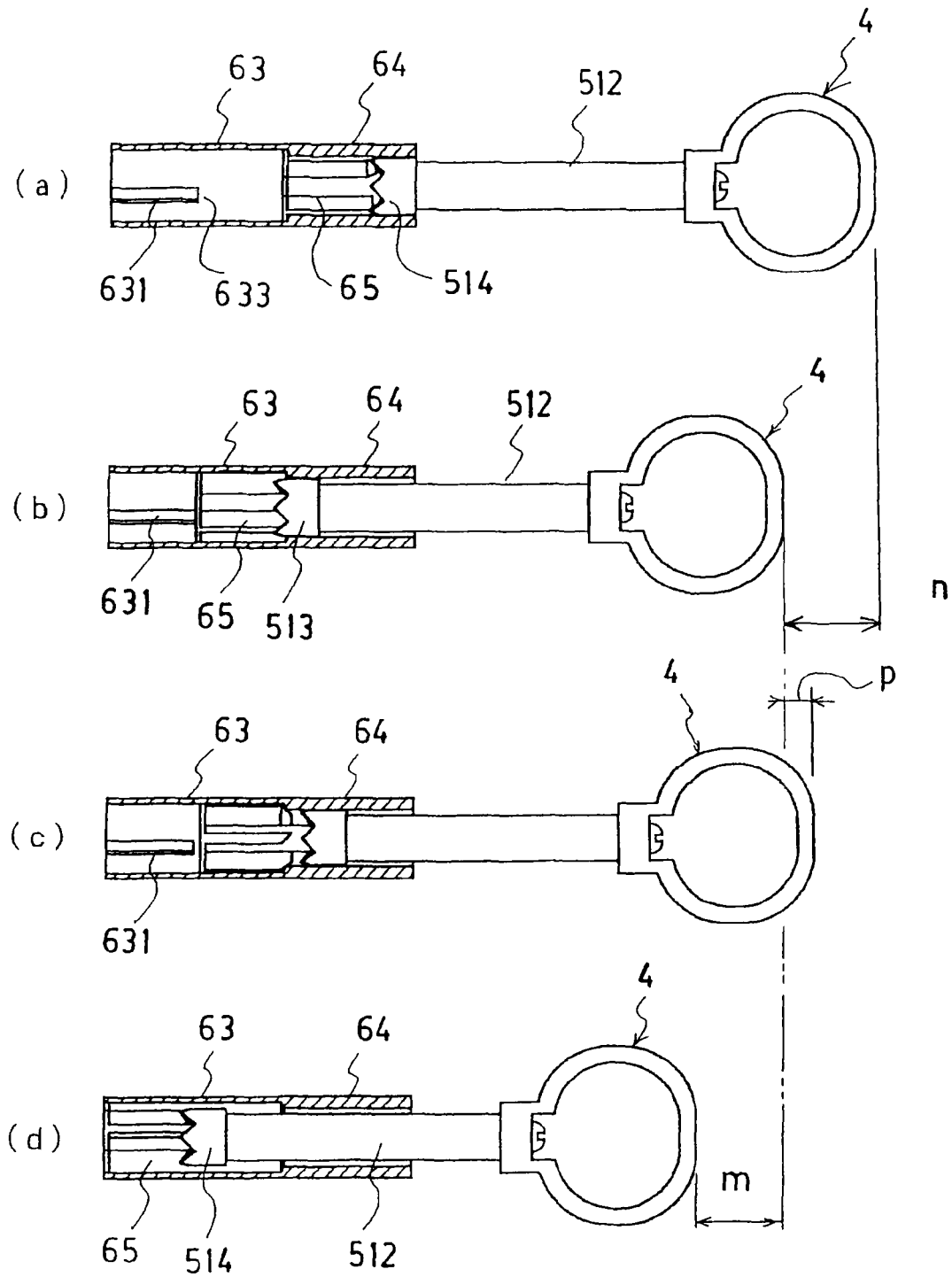
FIG. 22 is a longitudinal cross-sectional view for explaining each operating step of a clipping equipment of the present example.
Figure 23:
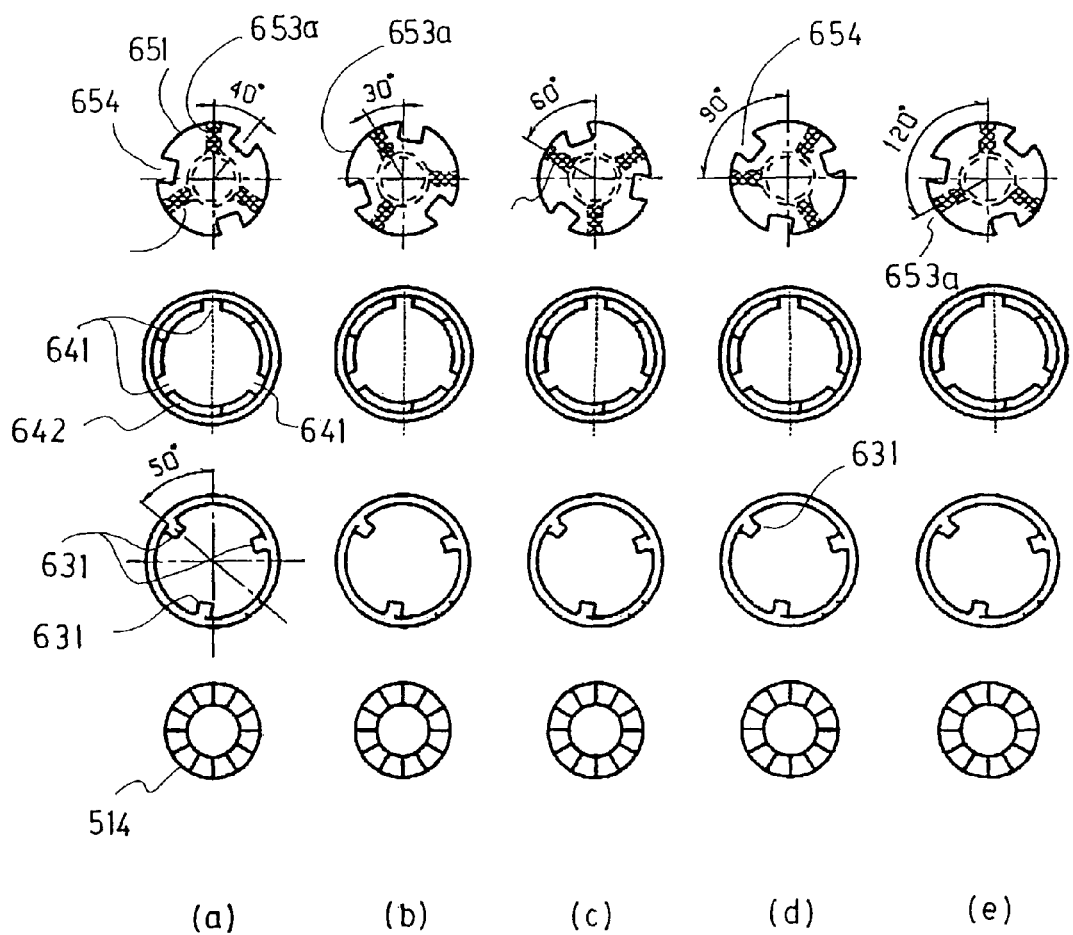
FIG. 23 is a view for explaining movement of a rotation body.
Figure 24:
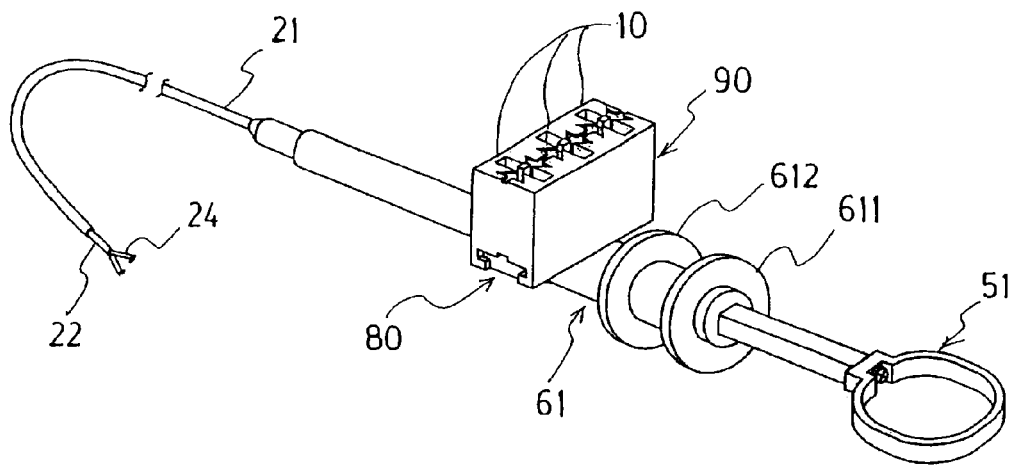
FIG. 24 is a perspective of a clipping equipment for a biological tissue in a third embodiment.
Figure 25:
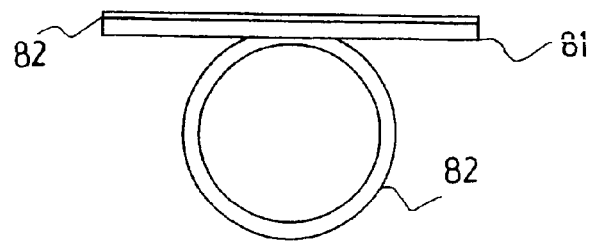
FIG. 25 is a front view of a mounting equipment which is mounted on a clipping equipment for a biological tissue of the present example.
Figure 26:
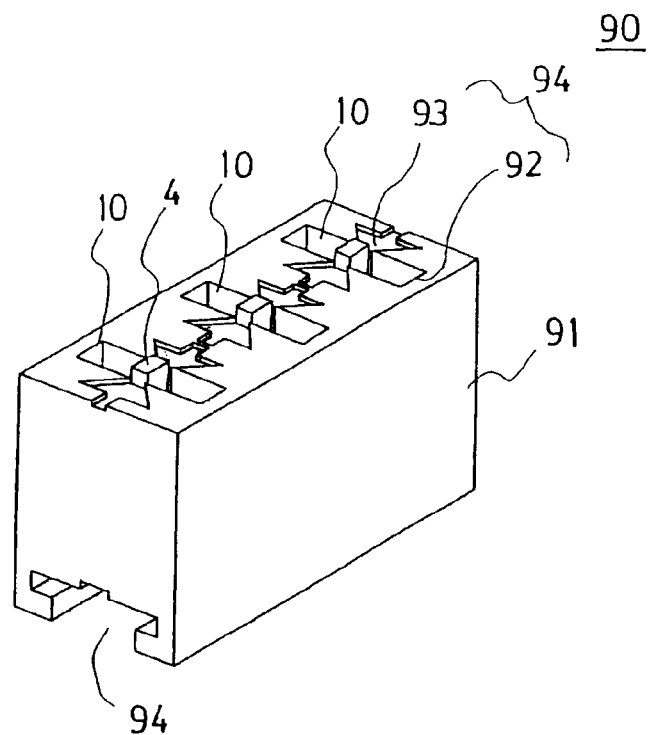
FIG. 26 is a perspective of a clip holder.
Figure 27:
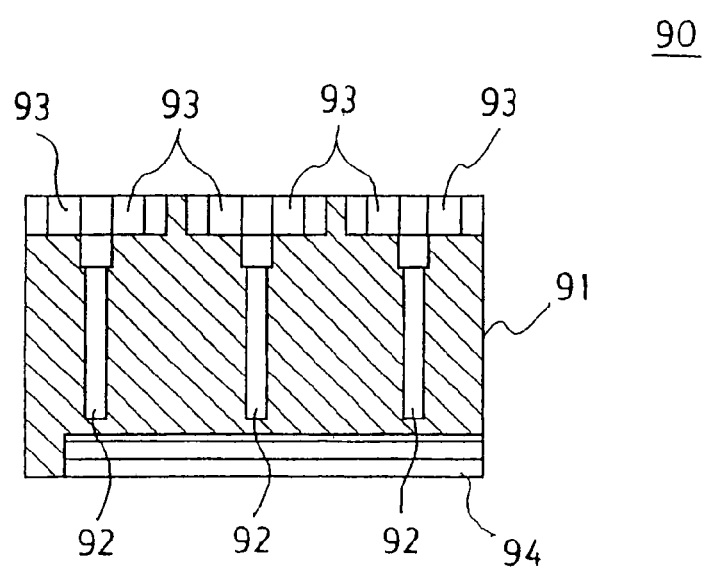
FIG. 27 is a cross-sectional view of a clip holding member.

Then, a method of operating a clipping equipment 30 of a second embodiment example will be explained below by referring to mainly FIG. 22 and FIG. 23. A method of operating a clipping equipment 30 comprises first forcing operation, retaining step, second forcing operation and returning step. In first forcing operation, when a handle 51 is pushed, a first cam part 514 at a tip of a handle and a second cam part 654 of a rotation body 65 are abutted (FIG. 22 (a) and FIG. 23 (a)). In this case, a first cam part 514 and a second cam part 654 are arranged so that mutual mountain-like top parts of cam parts are slightly slipped. Therefore, a mountain-like top part 515 of a first cam part 514 at a tip of a handle is forwarded while abutting against a mountain-like inclination of a second cam part 654 of a rotation body. And, a rotation body 65 is forwarded from a position retaining means 64 to a stopping means 63. When a rotation body 65 enters a stopping means 63, a first cam part 514 and a second cam part 654 are completely engaged, and a rotation body 65 is rotated from an original position by 30 degree counterclockwisely (first rotation). In this state, since a substrate 651 of a rotation body is in a relation that the substrate is abutted with a rib 631 of a stopping means 63, a rotation body 65 is moved by a stroke n, runs against an end face of a rib 631, and is stopped (FIG. 22(b) and FIG. 23(b)). By first forcing operation, an operating member 22 of a bar-like member 71 which is interlocked with movement of a rotation 65 is forwarded, a holder 24 is pulled into an operation member 22 to close a tip of a holder 24, making a holder 24 retain a clip 10a (FIG. 5).

In a retaining step, after first forcing operation, when a hand is released from a handle 51, a rotation body 65 is retreated by an elastic force of a spring 74, and a second cam part of a rotation body 65 and a cam groove 642 of a position retaining means are engaged. Thereupon, a tip of a second cam part of a rotation part 65 is rotated from an original position by 60 degree counterclockwisely along with inclination of saw blade-like cam groove 642 (second rotation), and is stopped in a valley part of a cam groove 642 (FIG. 22(c) and FIG. 23(c)). Thereby, the state where an opened clip 10a is retained at a tip of a holder 24 can be maintained. In addition, since an opening degree of a clip 10a is constant, position adjustment by fine handle procedure becomes unnecessary.

In second forcing operation, when a handle 51 is pushed from the retention state, a first cam part 514 of a handle axis and a second cam part of a rotation body are engaged, and a rotation body 65 is further rotated from an original position by 90 degree (third position). In this state, a notch part 654 of a rotation part 65 and a rib 631 of a stopping means 63 are in a fitting positional relationship. In this state, when a handle 51 is forced, a rotation body 65 is forwarded to a tip of a stopping means 63 (FIG. 22 (d) and FIG. 23 (d)). By second forcing operation, an operating member 22 of a bar-like member 71 which is interlocked with movement of a rotation body 65 is further forwarded by a stroke m, closing a clipping part 15 of a clip 10a (FIG. 6).

In a returning step, after second forcing operation, when a hand is released from a handle 51, an operating member 22 is returned by elastic action of a spring 74 and, interlocking therewith, fitting between a rotation body 65, a feather member 653, and a rib 631 of a stopping means 63 is released, a tip of a rotation body 65 comes to a spiral cam groove 642, is further moved along with its inclination, and is stopped at a valley part, rotating from an original position by 120 degree counterclockwisely (forth rotation). In this state, a feather member 653 of a rotation body 65 and a groove 641 of a position retaining means 64 are positioned so that they are fitted. For this reason, a rotation body 65 is automatically returned to an original position. Since by a returning step, an operating member 22 is returned to an original position, a tip of a self-opening holder is opened, and a clip 10a is detached from a holder 24. On the other hand, a clip of 10a is still closed, and mounting of a biological tissue on a clip 10a is completed.

In a clipping equipment 30 of a second embodiment example, an operating method is not limited to the aforementioned method of fixing an operating wire 23, and moving an operating member 22 by seeing relatively, but by reversing a position of a spring, and directions of a rotation body, a stopping means, and a position retaining means, an operation member may be fixed, and an operating wire may be moved. Alternatively, by changing shapes of a rotation body, a stopping means, and a position retaining means, multi-stage stoppage, and position retaining may be performed.

According to a clipping equipment 30 of a second embodiment example, when ligation and excision of a bleeding site of a biological tissue with an endoscope are performed, since it is not necessary to see an extent of opening of a clip with an endoscope, and fine position adjustment with handle operation becomes unnecessary, a treatment time can be shortened. Alternatively, by imparting a stoppage position having a constant moving distance, a tip of an endoscope treating equipment can be put in and out by a constant amount.

Then, a clipping equipment in accordance with a third embodiment will be explained by referring to FIG. 24 to FIG. 31. In a clipping equipment 40 in a third embodiment, the same symbol is added to the same component as that of the clipping equipment 30 in a second embodiment, explanation thereof will be omitted, and different points will be mainly explained. That is, a different point from a clipping equipment 30 in a clipping equipment 40 is in that a clip retaining member 90 is attached to an external circumferential surface of an equipment body part 61 near a second flange 612. A clip retaining member 90 is a block body 91, and has three of clip accommodating grooves 92 for accommodating a tip of a clip 10 downwardly in the sunk state, and generally cross grooves 94 consisting of guide grooves 93 which run straight through a center of an accommodating group 92, in a direction orthogonal with an accommodating groove 92. In addition, an engaging groove 94 which engages with a mounting equipment 80 is formed on a back of a block body 91. By closing one end of an engaging groove 94 to be a wall, positioning becomes easy. That is, when a plate-like engaging piece 81 of a mounting equipment is completely engaged with an engaging groove 94, a clip retaining member 90 is situated approximately at a center of an equipment body part 61.

A clip accommodating groove 92 is slightly larger than a plate width of a twin-arm part 11, and is slightly wider from a deepest part towards a surface. A depth of a clip accommodating groove 92 is such a depth that a basal part is slightly seen in the state where a clip 10 is accommodated, and a groove length of clip accommodating groove 92 is slightly smaller than a width by which a clip 10 is opened in the natural state. Thereby, upon accommodation of a clip 10 in an accommodating groove 92, since a twin-arm part is slightly closed, stable accommodation is possible. A shape of a guide groove 93 is not particularly limited, but in the present example, by adopting an alloy-shaped groove when seen in a plane surface, a tip hook 28 of a holder 24 is easily guided to a generally U-shaped part 41 of a basal part of a clip. A guide groove 93 colored with a light emitting paint is preferable in that a guide groove 93 can be recognized even in a dark endoscope chamber. The number of clip accommodating grooves 92 which are formed into a block body 91 is 1, 2 or 4 or more in addition to the aforementioned 3. A material for a clip retaining member 90 is not particularly limited, but when a transparent material is used, this is preferable in that weather a clip 10 is accommodated or not can be observed from the outside. Examples of a transparent material include a resin material such as acrylonitrile butadiene styrene resin (ABS resin), polyethylene, polystyrene, polycarbonate, and acryl resin. When a clip retaining member 90 is accommodated in a sterilized bag (not shown) in the state where a clip 10 is accommodated in an accommodating groove 92, this is preferable in that it is not necessary to perform sterilization treatment every operation, and operating property is excellent.

A mounting equipment 80 is an adapter for attaching a clip holding member 90 to a cylindrical body of an equipment body part 61. A mounting equipment 80 consists of a ring part 82 which is mounted on a equipment body part 61, and a plate-like engaging piece 82 which engages with an engaging groove 94 of a clip holding member 90 having a jaw part 82 provided above a ring part 82.

Figure 28:
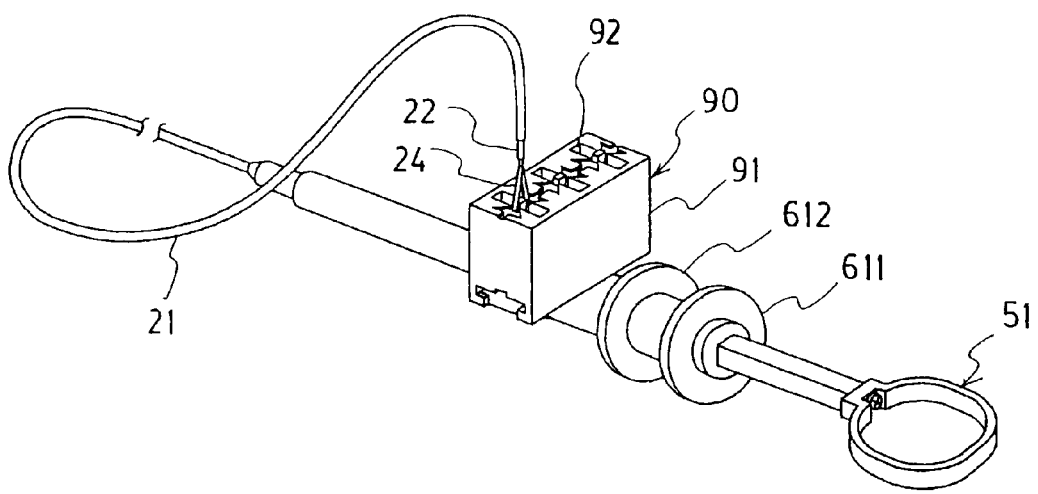
FIG. 28 is a view for explaining a method of using a clipping equipment for a biological tissue of the present example.

Then, a method of performing hemostasis using a clipping equipment 40 will be explained by referring to FIG. 28 to FIG. 31. In FIG. 28, description of a flange 213 of a sliding cylinder 211 is omitted. First, a clip holding member 90 is removed from a sterilized bag in the state where a clip 10 is accommodated in an accommodating groove 92, and is fixed to an equipment body part 61. While a tip part of an external casing 21 is grasped by a hand, a tip of a holder 24 is pushed against a guide groove 93 of a clip holding member 90. In this case, since a hand is not directly contacted with a clip 10, there is no fear of pollution.

Figure 29:
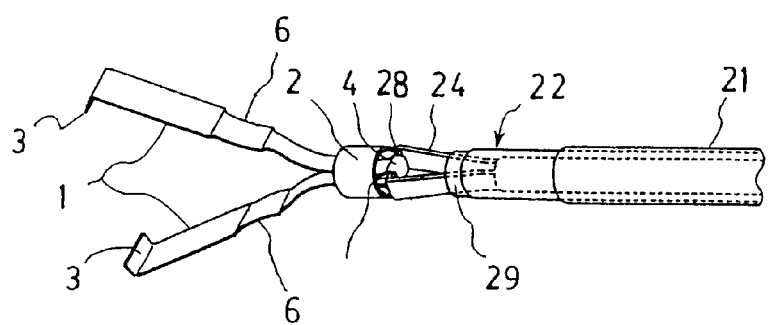
FIG. 29 is a view showing the state where a clip is held.

Then, when first forcing operation is performed by pushing a handle 51, an operating member 22 is forwarded, a tip of holder 24 provided at a tip of an operating wire 23 is closed, and a basal part 4 of a clip 10 is held (FIG. 28, FIG. 29). This operation can be simply operated only by grasping a handle 51 by one hand, and grasping an outer tube 21 by the other hand. In addition, by simple operation of forcing a tip of a holder 24 into a guide groove 93, a clip 10 can be attached to a holder 24. At a tip side of an operating member 22, a ring part 29 abutting against a securing ring 2 is provided. An external diameter of a ring part 29 is approximately the same as an external diameter of a securing ring 2, and a securing ring 2 can be forwarded by forwarding an operating member 22.

Figure 30:
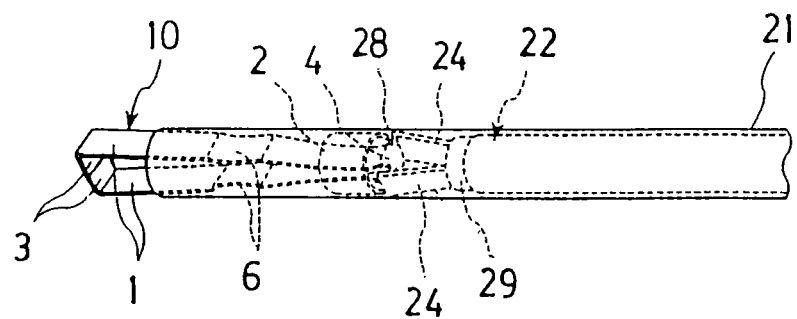
FIG. 30 is a view showing the state where a clip is accommodated in an external casing.
Figure 31:
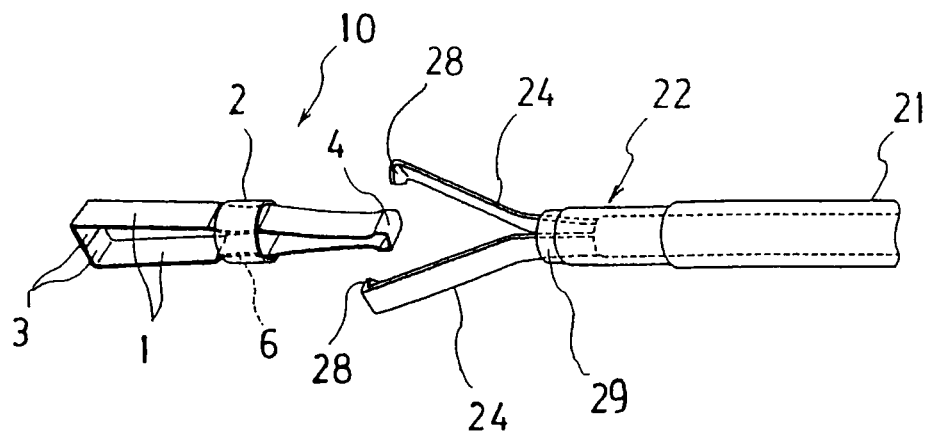
FIG. 31 is a view showing the state where a clip having a closed tip is detached from a holder.

In this state, engagement between an equipment body part 61 and a sliding cylinder 211 is released, and a handle 51 is pulled towards a basal side. Thereby, an operating member 22 is pulled towards a basal side relative to an external casing 21, and a clip 10 is transiently accommodated in an external casing 21 in the state where a tip thereof is closed (FIG. 30). In this state, an external casing 21 is passed through an endoscope (not shown), and a whole endoscope is inserted near a bleeding site in a living body. And, while an endoscope is confirmed, an external casing 21 is protruded from a tip of an endoscope. Then, when a handle 51 is pushed into a tip side, since an operating member 22 is forwarded relative to an external casing 21, a clip 10 is protruded from an external casing 21, and a tip becomes in the opened state. Then, a clop 10 having an opened tip is pushed against an objective site. And, when second forcing operation is performed by further pushing a handle 51, an operating member 22 is forwarded to push a securing ring 2 of a clip towards a tip side. Thereby, a securing ring 2 is engaged with a second concave part 6 of a clip 10, to clip an objective site of a living body. Since a securing ring 2 which has been pushed out by an operating member 22 is engaged with a second concave part 6, the closed state of a clip is maintained. After a clip 10 is closed, when a hand is released from a handle 51, a handle 51 is returned to an original position by a returning mechanism. Thereupon, since an operating member 22 is also retreated, a holder 24 is opened, and a closed clip 10 can be detached from a holder 24 (FIG. 31). And, while a clip 10 is dwelled in a body, a holder 24 together with an endoscope is extracted from a body. When a site clipped with a clip 10 is necrotized, a clip 10 is naturally detached, and is excreted from a body.

Figure 32:
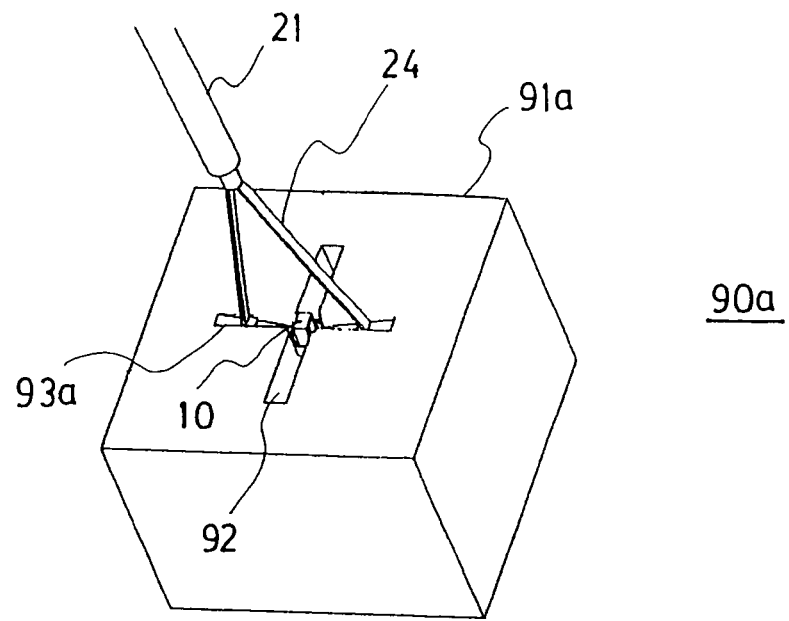
FIG. 32 is a perspective of other clip holder.
Figure 33:
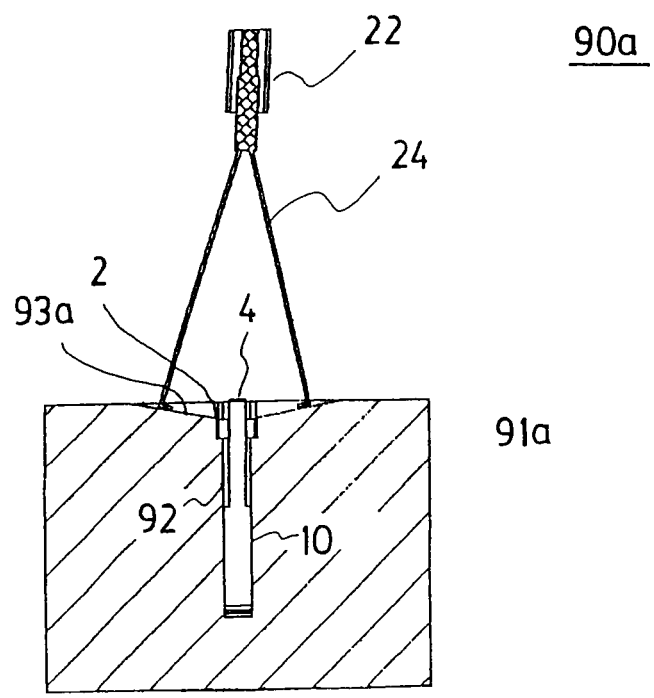
FIG. 33.
Figure 34:
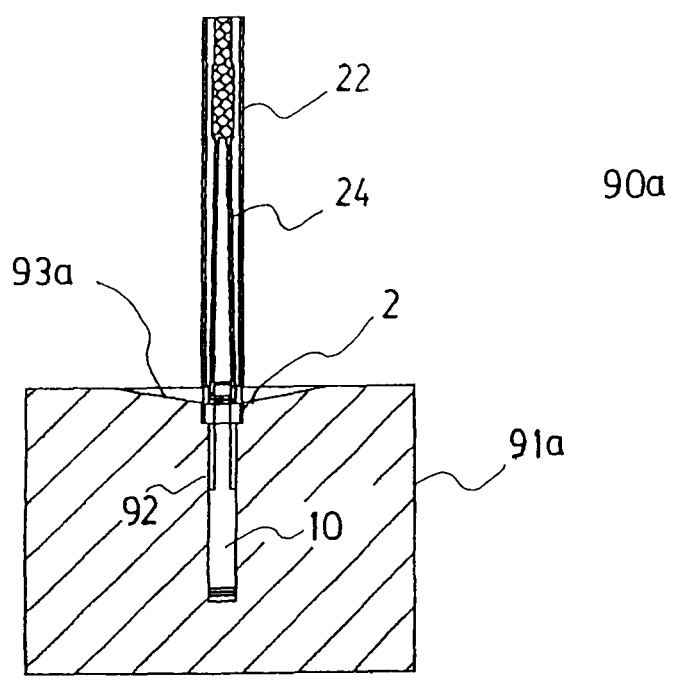
FIG. 34 are cross-sectional views for explaining a method of using other clip holder.
Figure 35:
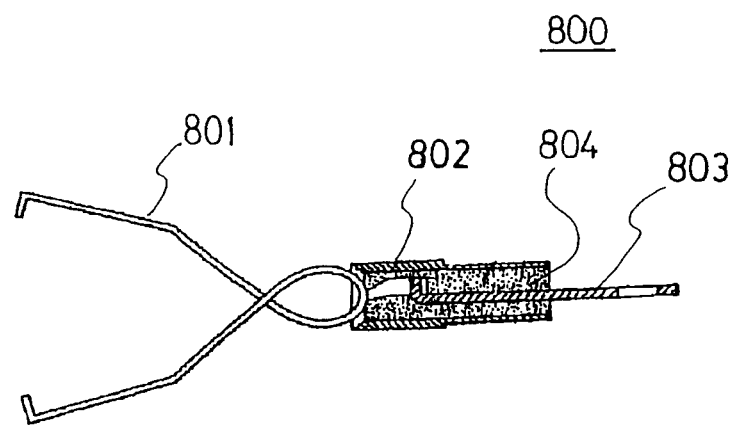
FIG. 35 is a cross-sectional view of a part of the previous clipping equipment.
Figure 36:
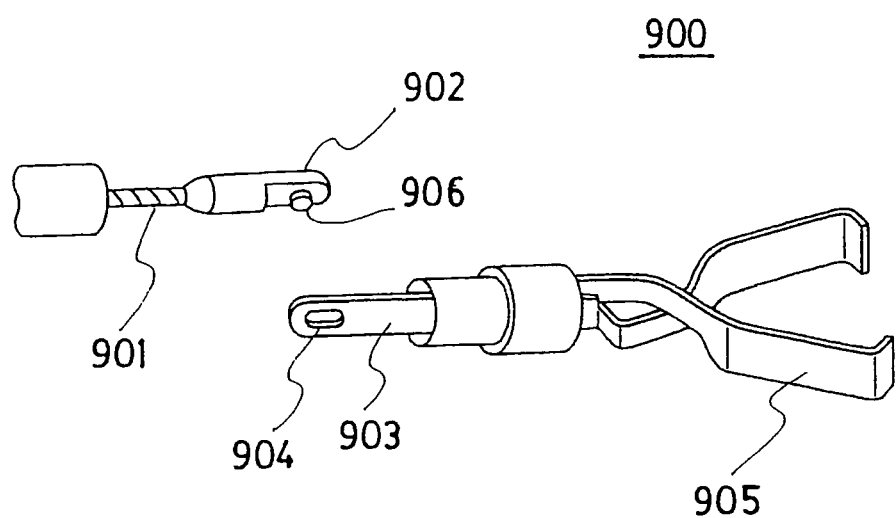
FIG. 36 is a perspective of a part of the previous other clipping equipment.

Then, a variation example of a clip holding member 90 will be explained by referring to FIG. 32 to FIG. 34. In a clip holding member 90a, the same symbol is added to the same component as that of a clip holding member 90, explanation thereof will be omitted, and different points will be mainly explained. That is, in a clip holding member 90a, a different point from a clip holding member 90 is a point in that the number of general cross grooves is one, a point in that a guide groove 93a is an inclination which runs straight passing through a center of an accommodating groove and descends towards a center, a depth at a central part of a guide groove is such that the central part is above a securing ring 2 in the state where a clip 10 is accommodated, and the holder is hung on a generally U-shaped basal part of the clip, and a point in that mounting is not on an external circumferential surface of an equipment body part 61, but on a separate member from a clipping equipment. Examples of a form of a guide groove 93 include a fan shape in addition to the aforementioned alloy shape and rectangular shape when seen on a plane surface.

Then, a method of removing a clip 10 accommodated in a clip holding member 90a will be explained. FIG. 33 is a cross-sectional view of FIG. 32, and FIG. 34 is a view showing the state where a holder 24 is closed in FIG. 33. A tip of a holder 24 is pushed against a guide groove 93a of a clip holding member 90a on which a clip 10 is mounted. In this state, by moving an operating member 22 to a clip holding member 90a side, the state where a clip 10 is held by a holder 24 is obtained (FIG. 34). Then, a clip 10 is removed from a clip holding member 90a, and mounting of a clip 10 on a clipping equipment is completed.

According to a clipping equipment 40 of a third embodiment example, the same operation as that of a clipping equipment 30 of a second embodiment example is performed and, additionally, by simple operation of grasping a handle 51 by one hand, grasping an external casing 21 by the other hand, and forcing a tip of a holder 24 into a guide groove 93, a clip 10 can be attached to a holder 24. For this reason, even an operator who is not familiar with this operation can perform clip mounting operation simply and efficiently.

INDUSTRIAL APPLICABILITY

The clip and the clipping equipment of the present invention are extremely useful as a treating equipment which is used in ligating a bleeding site of a biological tissue, stitching a laceration, and marking in excision of a mucosal tissue with an endoscope.

The invention claimed is:

1. A clipping equipment for clipping a biological tissue, comprising:
    a clip comprising:
        a self-opening clip body having a clipping part and a twin-arm part extending from a basal part, and
        a securing ring, wherein the self-opening clip body has a first concave part on a clip basal end, and a second concave part between the first concave part and a clip tip part, respectively, and the securing ring is mounted in the first concave part and is slidably movable with an external force from a mounting position in the first concave part to be mounted in the second concave part; and
    a device configured to close the clipping part of the self-opening clip body, comprising:
        an external casing which can be inserted into a biological cavity,
        an operating member configured to freely pass through the external casing,
        an operating wire configured to freely pass through the operating member, and
        a self-opening holder which can be opened and closed by the action of the operating member attached to a tip of the operating wire, wherein the clip is configured to be held by the self opening holder,
        a handle axis which is configured to be manually forwarded and retreated and includes a first cam part at a tip of the handle axis,
        a cylindrical position retaining means having a cam groove on a circumferential edge of an opening on a tip of the cylindrical position retaining means, and having a fitting groove extending on an internal circumferential surface in an axial direction of the cylindrical position retaining means,
        a cylindrical stopping means having a rib which is situated on a tip of the cylindrical stopping means at a side of the position retaining means and extends on an internal circumferential surface of the cylindrical stopping means from the tip side to a midway position in an axial direction of the cylindrical stopping means,
        a rotation body which is fitted with a first cam part of the handle axis, within the position retaining means and within the stopping means, and is configured to move in an axial direction by manual movement of the handle axis, and
        a spring for imparting spring power against forwarding of a handle.

2. The clipping equipment for a biological tissue according to claim 1, wherein the rotation body comprises:
    a substrate having notches provided on a circumferential edge of the substrate at an equivalent pitch angle, and a second cam part in which one end of a plate-like feather member extends in an axial direction and is provided between the notches at an equivalent pitch angle and which has a sharp cross sectional shape, on the substrate.

3. The clipping equipment for a biological tissue according to claim 2, further comprising:
a handle for controlling the operating member,
a first forcing mechanism for forwarding the handle and stopping forwarding of the handle,
a retaining mechanism for retaining a stoppage position of the handle once,
a second forcing mechanism for further forwarding the handle from its stoppage position, and stopping forwarding of the handle, and
a returning mechanism for automatically returning the handle to a position before first forcing, wherein the first forcing mechanism is configured such that a rotation body mounted on a position retaining means is moved from the position retaining means to a stopping means by forwarding a handle axis by handle operation, and is stopped by abutment between the rotation body and a rib end face of the stopping means.

4. The clipping equipment for a biological tissue according to claim 3, wherein the first forcing mechanism is configured such that the operating member is forwarded, and a holder is pulled into a cavity of the operating member to close a tip of the holder, making the holder hold the clip.

5. The clipping equipment for a biological tissue according to claim 1, further comprising:
a handle for controlling the operating member,
a first forcing mechanism for forwarding the handle and stopping forwarding of the handle,
a retaining mechanism for retaining a stoppage position of the handle once,
a second forcing mechanism for further forwarding the handle from its stoppage position, and stopping forwarding of the handle, and
a returning mechanism for automatically returning the handle to a position before first forcing, wherein the retaining mechanism is configured such that a rotation body is retreated by an elastic force of the spring, and is stopped by engagement between a second cam part of a rotation body and the cam groove of a position retaining means.

6. The clipping equipment for a biological tissue according to claim 1,
further comprising:
a handle for controlling the operating member,
a first forcing mechanism for forwarding the handle and stopping forwarding of the handle,
a retaining mechanism for retaining a stoppage position of the handle once,
a second forcing mechanism for further forwarding the handle from its stoppage position, and stopping forwarding of the handle, and
a returning mechanism for automatically returning the handle to a position before first forcing, wherein the second forcing mechanism is configured such that a first cam part of the handle axis and a second cam part of a rotation body are fitted, and the notch of a rotation body is fitted with a rib of the stopping means, thereby, a rotation body is forwarded to a tip of a stopping means.

7. The clip equipment for a biological tissue according to claim 6, wherein the second forcing mechanism is configured such that the operating member is further forwarded to close a clipping part of a clip.

* * * * *